United States Patent [19]

Fischer et al.

[11] Patent Number: 5,208,354

[45] Date of Patent: May 4, 1993

[54] PHOTOCHROMIC NAPHTHACENEQUINONES, PROCESS FOR THEIR PREPARATION AND THE USE THEREOF

[75] Inventors: Walter Fischer, Reinach, Switzerland; Jürgen Finter, Freiburg, Fed. Rep. of Germany; Heinz Spahni, Frenkendorf, Switzerland

[73] Assignee: Ciba-Geigy Corp., Ardsley, N.Y.

[21] Appl. No.: 801,150

[22] Filed: Dec. 2, 1991

[30] Foreign Application Priority Data

Dec. 5, 1990 [CH] Switzerland .................. 3837/90

[51] Int. Cl.$^5$ ...................... C07C 50/36; C07C 50/22
[52] U.S. Cl. ...................... 552/200; 552/201
[58] Field of Search ...................... 552/201, 200, 202

[56] References Cited

U.S. PATENT DOCUMENTS 4,036,805 7/1977 Tsujimoto et al. .

FOREIGN PATENT DOCUMENTS 438376 7/1991 European Pat. Off. .
2337855 2/1974 Fed. Rep. of Germany .

OTHER PUBLICATIONS

Chem. Abst. vol. 94, No. 7, 47012m (1980).
Y. E. Gerasimenko et al., Zhurnal Organicheskoi Khimii, vol. 7, No. 11, pp. 2413-2415 (1971).
Y. E. Gerasimenko et al., Zhurnal Organicheskoi Khimii, vol. 16, No. 9, pp. 1938-1945 (1980).

Primary Examiner—Marianne M. Cintins
Assistant Examiner—Kimberly J. Kestler
Attorney, Agent, or Firm—Kevin T. Mansfield; George R. Dohmann

[57] ABSTRACT

Compounds of formula I or V or mixtures thereof

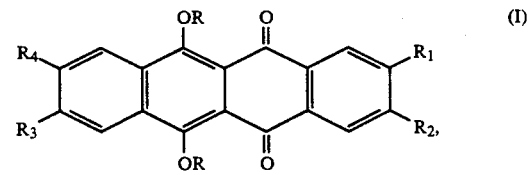

wherein
R is unsubstituted $C_6$-$C_{14}$aryl or $C_6$-$C_{14}$aryl which is substituted by $C_1$-$C_{12}$alkyl, $C_1$-$C_{12}$alkoxy, $C_1$-$C_{12}$alkylthio, phenyl, benzyl, —CN, —CF$_3$, halogen or —COOR$_5$, and R$_5$ is H, $C_1$-$C_{18}$alkyl, cyclohexyl, cyclopentyl, phenyl, $C_1$-$C_{12}$alkylphenyl, benzyl or $C_1$-$C_{12}$alkylbenzyl, and at least one of the substituents R$_1$ to R$_4$ is —F, —Cl or —Br, or is independently the group RO—, and the other substituents R$_1$ to R$_4$ are H, —F, —Cl or —Br, are reversible photochromic systems which can be used for contrast formation, light absorption or for the reversible optical storage of information.

9 Claims, No Drawings

PHOTOCHROMIC NAPHTHACENEQUINONES, PROCESS FOR THEIR PREPARATION AND THE USE THEREOF

The present invention relates to naphthacene-6,11- and naphthacene-5,12-diones which are substituted in positions 5,12 and 6,11 by aryloxy groups, and in positions 2,3,8 and/or 9 by at least one phenoxy group or at least one fluorine, chlorine or bromine atom, to corresponding 5,12- and 6,11-dichloronaphthacenediones, to a process for their preparation and to the use thereof as photochromic systems for contrast formation, light absorption or for recording information.

In Zhurnal Organicheskoi Khimii, Vol. 7, No. 11, pp. 2413-2415 (1971), Yu. E. Gerasimenko et al. describe 6-phenoxynaphthacene-5,12-dione as a reversible photochromic compound which, when subjected to irradiation with light, forms the orange 5-phenoxynaphthacene-6,12-dione (anaquinone). In Zhurnal Organicheskoi Khimii, Vol. 16, No. 9, pp. 1938-1945 (1980), Yu. E. Gerasimenko et al. describe 6,11-diphenoxynaphthacene-5,12-dione, whose photoisomerisation is used for synthesising 6-amino derivatives of 12-phenoxynaphtacene-5,11-dione.

In one of its aspects, the present invention relates to compounds of formula I, or mixtures thereof,

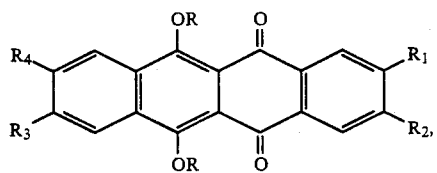

wherein

R is unsubstituted $C_6$-$C_{14}$aryl or $C_6$-$C_{14}$aryl which is substituted by $C_1$-$C_{12}$alkyl, $C_1$-$C_{12}$alkoxy, $C_1$-$C_{12}$alkylthiol, phenyl, benzyl, —CN, —CF$_3$, halogen or —COOR$_5$, and R$_5$ is H, $C_1$-$C_{18}$alkyl, cyclohexyl, cyclopentyl, phenyl, $C_1$-$C_{12}$alkylphenyl, benzyl or $C_1$-$C_{12}$alkylbenzyl, and at least one of the substituents R$_1$ to R$_4$ is —F, —Cl or —Br, or is independently the group RO—, and the other substituents R$_1$ to R$_4$ are —H, —F, —Cl or —Br.

R in formula I is preferably unsubstituted or substituted $C_6$-$C_{10}$aryl such as phenyl, or 1-or 2-naphthyl. Preferably R is unsubstitued or substituted phenyl.

The group R may be substituted by one or more, preferably by 1 to 3, substituents. If R is substituted by alkyl, alkoxy or alkylthiol, these radicals may be linear or branched and preferably contain 1 to 6, most preferably 1 to 4, carbon atoms. Exemplary of such radicals are methyl, ethyl, the isomers of propyl, butyl, pentyl, hexyl, heptyl, octyl, nonyl, decyl, and the corresponding alkoxy and alkylthio radicals. Preferred radicals are methyl, ethyl, n- and isopropyl, n-, iso- and tert-butyl, methoxy, ethoxy, methylthio and ethylthio.

If R is substituted by halogen, preferred halogens are bromo, chloro and fluoro.

R$_5$ as alkyl may be linear or branched. Further examples of the alkyl radicals mentioned above are the isomers of tridecyl, tetradecyl, pentadecyl, hexadecyl, heptadecyl and octadecyl. R$_5$ as alkyl preferably contains 1 to 12, most preferably 1 to 6, carbon atoms. R$_5$ as alkylphenyl is preferably $C_1$-$C_6$alkylphenyl, most preferably $C_1$-$C_4$alkylphenyl, for example dodecylphenyl, octylphenyl, hexylphenyl, n-, iso- or tert-butylphenyl, n- or iso-propylphenyl, ethylphenyl or methylphenyl. R$_5$ as alkylbenzyl is preferably $C_1$-$C_6$alkylbenzyl, most preferably $C_1$-$C_4$alkylbenzyl, for example dodecylbenzyl, octylbenzyl, hexylbenzyl, n-, iso- or tert-butylphenyl, n- or isopropylbenzyl, ethylbenzyl or methylbenzyl. R$_5$ is preferably H or $C_1$-$C_{18}$alkyl, most preferably $C_1$-$C_{12}$alkyl.

In a preferred embodiment of the invention, R in formula I is unsubstituted or substituted by $C_1$-$C_4$alkyl, $C_1$-$C_4$alkoxy, $C_1$-$C_4$alkylthio, —F, —Cl, —Br or —COOR$_5$, and R$_5$ is H or $C_1$-$C_{18}$alkyl.

In a particularly preferred embodiment of the invention, R in formula I is —COO($C_1$-$C_6$)alkyl which is unsubstituted or substituted by —Cl or —Br.

Another preferred embodiment of the invention relates to those compounds of formula I, wherein at least one of the substituents R$_1$ to R$_4$ is a group RO— or —F, —Cl or —Br, and the other substituents R$_1$ to R$_4$ are —H.

In yet a further preferred embodiment of the invention, R$_1$ or R$_4$, or R$_1$ and R$_3$ or R$_4$, or R$_1$ and R$_2$, or R$_1$ to R$_4$ are a group RO—, —F, —Cl or —Br, most preferably a group RO— or Cl.

Preferred compounds of formula I are those wherein R is unsubstituted phenyl.

Particularly preferred compounds of formula I are 6,11-diphenoxy-2-chloronaphthacene-5,12-dione, 2,6,11-triphenoxynaphthacene-5,12-dione, 6,11-diphenoxy-2,3,8,9-tetrachloronaphthacene-5,12-dione and 2,3,6,8,9,11-hexaphenoxynaphthacene-5,12-dione.

In another of its aspects, the invention relates to a process for the preparation of compounds of formula I, which comprises reacting 1 mol of a compound of formula II

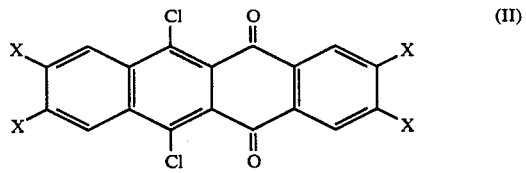

wherein at least one of the substituents X is —F, —Cl or —Br, and the other substituents X are —H, —F, —Cl or —Br, in the presence of a polar aprotic solvent and at elevated temperature, with at least 2 mol of a compound of formula RO⊖M⊕, wherein R is as previously defined and M is an alkali metal or tertiary ammonium containing 3 to 18 carbon atoms.

Surprisingly, it has been found that both chlorine atoms can be substituted regioselectively by phenoxy groups even if the naphthacene ring system contains further halogen atoms.

The process of the invention is preferably carried out in the temperature range from 50° to 200° C., most preferably from 50° to 150° C. The salts of formula RO⊖M⊕ may be used as such or produced in situ in the reaction mixture by reacting a suitable phenol with an alkali metal base or an alkali metal carbonate. The salts can be used in equimolar amounts or in excess, for example in an excess of up to 40 mol %, if it is desired to effect substitution of all halogen atoms.

Typical examples of suitable solvents are N-substituted carboxamides and lactams (such as dimethyl formamide or N-methylpyrrolidone), sulfoxides and sulfones (such as dimethyl sulfoxide, tetramethylene sulfone), or ethers (such as n-dipropyl ether, n-dibutyl ether, tetrahydrofuran or dioxane).

The compounds of formula I can be isolated and purified by conventional methods, for example by crystallisation and recrystallisation, or by chromatographic methods.

The compounds of formula RO⊖M⊕ are known or obtainable in known manner by reacting suitable phenols with alkali metal bases, alkali metal carbonates or tertiary amines. They can also be produced in the reaction mixture in situ. Particularly suitable alkali metal cations are Li⊕, Na⊕ and K⊕. Tertiary ammonium is typically trimethylammonium, triethylammonium, tri-n-propylammonium and tri-n-butylammonium.

The invention further relates to compounds of formula II

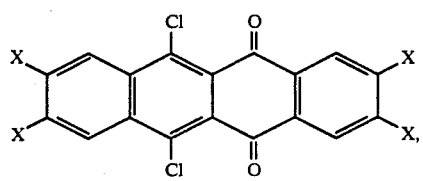

wherein at least one of the substituents X is —F, —Cl or —Br, and the other substituents X are —H, —F, —Cl or —Br. The preferred meanings of X are the same as those given for $R_1$ to $R_4$ defined as —H, —F, —Cl and —Br in the compounds of formula I.

The compounds of formula II are obtainable by the following process:

The reaction of the known compounds of formula III

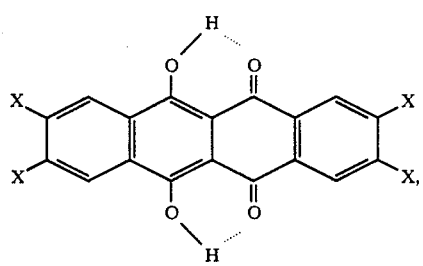

wherein X is as defined in formula II, with a chlorinating agent, typically $POCl_3$, gives the compounds of formula IV which, when unsymmetrically substituted, are obtained as a mixture of position isomers of formulae IV and IVa:

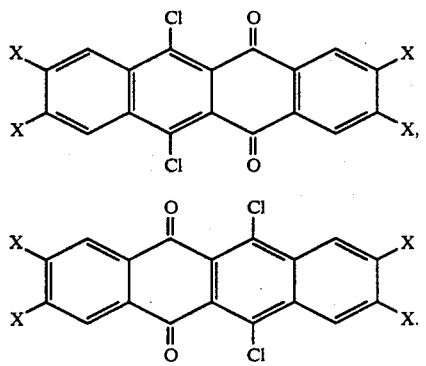

These mixtures can be used direct for the preparation of compounds of formula II or separated beforehand, for example by chromatographic methods. The compounds of formula III are obtainable in a manner known per se for example, by reacting appropriately halogenated or non-halogenated phthalic anhydrides with appropriately halogenated or non-halogenated 1,4-dihydroxynaphthalene, in the presence of $B_2O_3$, at elevated temperature.

The compounds of formula I are crystalline, thermally stable and light-yellow to yellowish-orange in colour. They are soluble in organic solvents. They are effective photoinitiators and photosensitisers for photopolymerisable systems which contain ethylenically unsaturated double bonds. Further, the compounds of formula I are reversibly photochromic compounds which, when irradiated, undergo a marked colour change from yellow to yellowish-orange to orange to red.

When the compounds of formula I are irradiated, alone or incorporated in a substrate, with light having a wavelength of ca. 300 to 450 nm, a pronounced change in colour towards orange to red is observed. In comparison with 6,11-diphenoxynaphthacene-5,12-dione, the light absorption is displaced to a higher wavelength. The change in colour derives from the photochemical conversion of the paraquinones of this invention into the corresponding anaquinones of formula V. The rate of conversion is surprisingly high and, depending on the amount, thickness of the sample and irradiation intensity, can be less than 3 seconds.

The invention further relates to the anaquinones of formula V

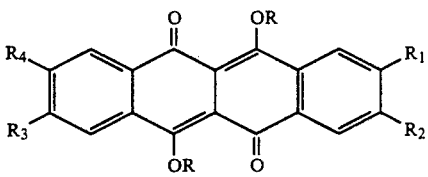

wherein R, $R_1$, $R_2$, $R_3$ and $R_4$ are as previously defined, including the preferred meanings.

The compounds of formula V can be obtained, after irradiating solutions of the compounds of formula I, by removing the solvent, and, as required, purified by conventional methods.

The change in colour is reversible. Renewed irradiation with light having a wavelength of ca. 450 to 550 nm gives the original colour (reformation of the paraquinone structure). It is especially advantageous that this procedure can be repeated several times. The stability of the photochemical conversion of paraquinones to anaquinones and the reverse reaction to paraquinones is surprisingly high and the fatigue even in air or in substrates is correspondingly low. Thus virtually no changes are observed in more than 200 cycles. It is also advantageous that the light absorption necessary for the photochemical conversion lies in the range of the wavelength of commercially available lasers.

The invention further relates to the use of compounds of formula I or V, or mixtures thereof, as reversible photochromic structures for contrast formation or light absorption.

The compounds of formula I can be used as photoinitiators and, preferably, as photosensitisers in photopolymerisible systems, in which case they act simultaneously as colour indicators. Thus it is possible to mark irradiated products (for example protective layers, printing plates, offset printing plates, printed circuits, solder masks) and to distinguish them from non-irradiated products and, in product control, to sort out imperfectly irradiated products before or after development.

The major advantage in using the compounds of formula I as colour indicators lies in the increase of the sensitiser action. Components normally used as colour change systems generally effect a diminution of the photosensitivity.

The compounds of formula I or V can also be used by themselves, in solution or incorporated in polymers, as photochemically modifiable colour indicators or as photochemically modifiable circuit components.

The compounds of formula I can also be used in organic or inorganic glass as photochemically modifiable colour filters, for example in glass for sunglasses, contact lenses, windows and mirrors.

The invention further relates to a radiation-sensitive composition comprising a) a radiation-sensitive organic material, and b) at least one compound of formula I or V or a mixture thereof.

The compounds of formulae I and V or mixtures thereof may be present in an amount of 0.001 to 20% by weight, preferably 0.001 to 10% by weight and, most preferably, 0.01 to 5% by weight, based on component a).

Radiation-sensitive and hence also photostructurable materials are known. They may be positive or negative systems. Such materials are described, for example, by E. Green et al. in J. Macromol. Sci.; Revs. Macromol. and Chem., C21(2), 187-273 (1981 to 1982) and by G. A. Delzenne in Adv. Photochem., 11, S. 1-103 (1979).

The radiation-sensitive organic material is preferably a1) a non-volatile monomeric, oligomeric or polymeric substrate containing photopolymerisable or photodimerisable ethylenically unsaturated groups, a2) a cationically curable system, or a3) photocrosslinkable polyimides.

Photopolymerisable substances are typically acrylates and, preferably, methacrylates of polyols, for example ethylene glycol, propanediol, butanediol, hexanediol, bis(hydroxymethyl)cyclohexane, polyoxyalkylenediols such as di-, tri- or tetraethylene glycol, di- or tri-1,2-propylene glycol, trimethylolmethane, trimethylolethane or trimethylolpropane and pentaerythritol, which may be used by themselves, in mixtures and in admixture with binders.

Exemplary of photodimerisable substances are homo- and copolymers which contain cinnamic acid groups or substituted maleimidyl compounds in side groups or chalcone groups in the polymer chain.

Preferred compositions are those wherein component a1) is a homo- or copolymer of acrylates, methacrylates or maleates whose ester groups contain a radical of formula

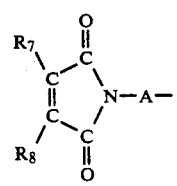

wherein A is linear or branched unsubstituted or hydroxyl-substituted $C_2$-$C_{12}$alkylene, cyclohexylene or phenylene, and $R_7$ and $R_8$ are each independently of the other chloro or bromo, phenyl or $C_1$-$C_4$alkyl, or $R_7$ and $R_8$, when taken together, are trimethylene, tetramethylene or

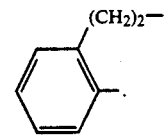

Such polymers are disclosed, for example, in U.S. Pat. No. 4,193,927.

The photopolymerisable or photodimerisable substances can contain further additives customarily used for processing or application, as well as other photoinitiators or photosensitisers.

The cationically curable systems are preferably epoxy compounds containing at least two epoxy groups in the molecule and in which a photoinitiator is incorporated. Suitable photoinitiators are typically cyclopentadienylarene metal salts, cyclopentadienyl metal carbonyl salts and onium salts which are described in the above mentioned publications. The curable systems may contain additives customarily used for processing and application.

Photosensitive polyimides are disclosed, for example, in DE-A-1 962 588, EP-A-0 132 221, EP-A-0 134 752, EP-A-0 162 017, EP-A-0 181 37 and EP-A-0 182 745.

The composition of this invention is applied by known methods as layer to substrates and either a protective layer is produced by irradiation over the surface, or a relief image is produced by irradiation through a photomask or by locally defined irradiation with a guided laser beam or by holographic methods and subsequent development.

In another of its aspects, the invention relates to a composition comprising a) a colourless organic solvent, a polymer or an organic glass or a compound glass, and b) dissolved, incorporated therein or present as layer on at least one surface, a compound of formula I or V or a mixture thereof. Component b) is preferably present in an amount of 0.001 to 20% by weight, preferably 0.001 to 10% by weight and most preferably, 0.01 to 5% by weight, based on component a). Organic solutions can be used for coating other substances, for example solid substrates such as inorganic glasses which can then be used as photochemically modifiable substrates. The compounds of formula I can also be sublimed on to substrates. The coated substrated can be provided with a protective layer of, for example, transparent polymers. Solid substrates can also be coated with compositions which contain a polymer and at least one compound of formula I or V. Suitable solvents are typically hydrocarbons, halogenated hydrocarbons, ketones, carboxylic acid esters and lactones, N-alkylated acid amides and lactams, alkanols and ethers.

Exemplary of suitable polymers are thermoset plastics, thermoplastics and structurally crosslinked polymers. The polymers are preferably transparent. Such polymers and organic glasses are known to those skilled in the art. The incorporation of the compounds of the invention is effected by known methods, for example by dissolving methods and removing the solvent, calendering or extrusion. The compounds of this invention can also be incorporated in the substrates before, during or after their synthesis.

The invention also relates to a process for the preparation of coloured materials under the influence of light, which comprises incorporating a compound of formula I or V in the material and then irradiating said material with light.

The invention further relates to the use of compounds of formula I as photosensitizers and colour indicators or photochemically modifiable colour filters under the influence of light.

In yet another of its aspects, the invention relates to the use of a compound of formula I or V for the reversible optical storage of information, which information is written with light, preferably laser light, into a memory-active layer containing said compound. The written information can be erased, preferably with laser light, thus affording the possibility of cyclic writing-in and erasing.

To produce a memory-active layer, the compound of formula I or V can be dissolved in a transparent matrix by methods desribed above and applied in a thin layer to a flat substrate. The thickness of the memory-active layer is ca. 0.1-100 μm, preferably 0.3-3 μm.

The information can be written by scanned, holographic or photographic irradiation of the memory-active layer with spectral, preferably coherent, laser light in the wavelength range of 440-550 nm, preferably 480-530 nm.

Reading out can be effected with reduced irradiation intensity at the wavelength in which the information is written via the locally altered transmission, reflectance, refraction or fluorescence of the memory-active layer.

Erasure can be made by pin-point or spread irradiation of the memory-active layer containing the compounds of formula I and/or V in the wavelength range of 300-450 nm, preferably 300-420 nm.

One advantage of the utility of this invention is that the wavelengths necessary for writing in, reading out and erasing are in the range of commercially available lasers (for example argon ion lasers: 488/514 nm and 351/363 nm; neodym-YAG lasers; 532 nm and 355 nm with frequency doubling and trebling; XeF excimer lasers: 351 nm; HeCd lasers: 325 and 442 nm).

A further advantage is the high contrast of absorption obtainable between the written and erased state in the range of 450-550 nm and the wide dynamic range associated therewith of the memory-active layer.

Another advantage is that the quantum yield when writing is fairly low, so that the danger of overwriting when reading out is greatly diminished.

Conversely, it is also advantageous that the quantum yield when erasing is fairly high, thus making possible a rapid erasure over a large area.

Yet a further advantage is that, when reading out, the compound fluoresces and hence makes possible a highly sensitive detection of the memory status via the fluorescence. The fact that the energy pulsed in for reading out dissipates substantially via the fluorescence and not thermally also counteracts an undesirable heating of the memory-active layer.

Another advantage is the high photochemical stability of the compound and the great number of writing/erasing cycles thereby obtainable.

Finally, yet another advantage is the possibility of cyclic data refreshing by admixture of a suitable quantum of light of the erasure wavelength during reading out.

The invention is illustrated by the following Examples.

A) PREPARATION OF THE STARTING COMPOUNDS

Example A1

2,3,6,8,9,11-Hexachloronaphthacene-5,12-dione 30 g (70 mmol) of 2,3,8,9-tetrachloro-6,11-dihydroxynaphthacene-5,12-dione, 60 ml of $POCl_3$ and 500 ml of o-dichlorobenzene are stirred for 90 hours under reflux. Excess $POCl_3$ is distilled off, together with the o-chlorobenzene, until the reaction volume is still about 300 ml. The precipitate is isolated by filtration from the cooled reaction mixture, washed repeatedly with water and aqueous sodium carbonate solution and dried. The dry product is stirred in cyclohexane, isolated by filtration and then dried, giving a yield of 28.6 g (88%), melting point (mp):>260° C.

Example A2

2-Fluoro- and 9-fluoro-6,11-dichloronaphthacene-5,12-dione (mixture of isomers)

3.0 g (9.73 mmol) of 2- and 9-fluoro-6,11-dihydroxynaphthacene-5,12-dione (mixture of position isomers), 4 ml of $POCl_3$ and 30 ml of o-dichlorobenzene are stirred for 10 hours under reflux. The reaction mixture is poured into water and neutralised with 2N aqueous NaOH. The precipitate is isolated by filtration, washed with water, dried, taken up in 400 ml of toluene. After addition of basic alumina, the batch is filtered hot. The filtrate is concentrated by evaporation, giving 1.57 g (47%) of the product mixture. Mass spectrum: 344, 346, 348 and 350 ($M^+$: base peak).

B) PREPARATION OF THE INVENTIVE COMPOUNDS

Example B1

2,3,8,9-Tetrachloro-6,11-diphenoxynaphthacene-5,12-dione 2.32 g (5 mmol) of the compound of Example A1, 1.41 g (15 mmol) of phenol, 4.15 g (30 mmol) of potassium carbonate and 100 ml of tetrahydrofuran are heated for 5 hours under reflux. The mixture is poured into water, with stirring, and then filtered. The precipitate is washed first with water and then with methanol/water, dried, and then recrystallised from o-dichlorobenzene, affording the title compound in a yield of 2.57 g (89%) in the form of yellow crystals with a melting point of 326°-329° C. Mass spectrum 578/580/582 ($M^+$: base peak).

When irradiated, a solution of the compound in toluene undergoes a reversible colour change from yellow to orange.

Example B2

2,3,6,8,9,11-Hexaphenoxynaphthacene-5,12-dione 1.5 g (3.2 mmol) of compound A1, 2.43 g (25.8 mmol) of phenol, 4.45 g (32.3 g) of potassium carbonate and 120 ml of N-methylpyrrolidone are stirred for 8 hours at 150° C. The mixture is taken up in tetrahydrofuran/toluene/2N hydrochloric acid and the organic phase is separated, washed with water, dried over sodium sulfate and then concentrated by evaporation. The crude product is dissolved in toluene and chromatographed over silica gel, affording the title compound in a yield of 0.65 g (25%) in the form of yellowish-orange crystals.

Mass spectrum: 810 (M+: base peak).

When irradiated, a solution of the compound in toluene undergoes a reversible colour change from yellowish-orange to red.

Example B3

Mixture of 2,6,11- and 6,9,11-triphenoxynaphthacene-5,12-dione 0.5 g (1.45 mmol) of compound A2, 0.8 g (5.8 mmol) of potassium carbonate, 0.48 g (5.07 mmol) of phenol and 5 ml of dimethyl sulfoxide are stirred for 4 hours at 100° C. The reaction mixture is poured into dilute hydrochloric acid and extracted with tetrahydrofuran/toluene (1:1). The extracts are washed with saturated aqueous NaCl and water, dried over sodium sulfate and concentrated by evaporation. Recrystallisation from toluene gives 0.58 g (75%) of the title compound of m.p.: 220°-23° C. Mass spectrum: 534 (M+: base peak).

When irradiated, a solution of the compound in toluene undergoes a reversible colour change from yellow to orange.

C) USE EXAMPLES

Example C1

2.5 g of polystyrene are dissolved in 15 ml of toluene at 60° C. under argon, To this solution are added, after 20 minutes. 25 mg of the compound of Example B1, and the mixture is stirred for 20 minutes. The solution is applied with a 200 μm doctor knife at 80° C. to a glass plate and then dried for 60 minutes at 80° C., to give a transparent film having a thickness of about 30 μm. The film is mounted on a quartz plate in the testing chamber of a spectrophotometer and irradiated with a 300 W xenon lamp through glass fibres and a UV filter. The irradiation is discontinued at 60 second intervals and the absorption spectrum is measured. The spectrum of the sample changes from yellow (optical density 1 at about 320 nm, 0.4 at about 400 nm and 0 above 450 nm) to red (absorption band in the range from about 400–450 nm; maximum optical density 0.65 at 480 nm). The time constant of the conversion is 140 seconds.

For the reverse reaction, the UV filter is replaced by a yellow cut-on filter (Schott GG 455). The integral irradiation intensity in the range from 430–540 is 3 mW/cm². The irradiation causes the long-wave absorption band to disappear at 400–450 nm to a maximum optical density of 0.2 at 480 nm. The time constant of the reverse reaction is 110 seconds. In further irradiation cycles these critical values of the optical density remain constant.

Example C2

The general procedure of Example C1 is repeated, except that the compound of Example B2 is used. The spectrum changes from yellow (optical density 1 at about 340 nm, 0.35 at about 400 nm and 0 above 450 nm) to red (maximum absorption 0.6 at 480–510 nm) with a time constant of 180 seconds. The time constant of the reverse reaction (irradiation intensity 2.5 mW/cm²) is 160 seconds (maximum optical density 0.15 at 480 nm).

What is claimed is:

1. A compound of formula I or a mixture thereof

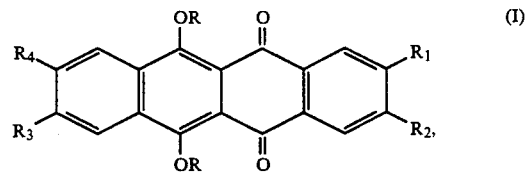

wherein

R is unsubstituted $C_6$–$C_{14}$aryl or $C_6$–$C_{14}$aryl which is substituted by $C_1$–$C_{12}$alkyl, $C_1$–$C_{12}$alkoxy, $C_1$–$C_{12}$alkylthio, phenyl, benzyl, —CN, —CF$_3$, halogen or —COOR$_5$, and R$_5$ is H, $C_1$–$C_{18}$alkyl, cyclohexyl, cyclopentyl, phenyl, $C_1$–$C_{12}$alkylphenyl, benzyl or $C_1$–$C_{12}$alkylbenzyl, wherein at least one of the substituents R$_1$ to R$_4$ is the group RO—, and the other substituents R$_1$ to R$_4$ are H, —F, —Cl or —Br.

2. A compound according to claim 1, wherein R in formula I is unsubstituted or substituted $C_6$–$C_{10}$aryl.

3. A compound according to claim 2, wherein R is unsubstituted or substituted phenyl or 1- or 2-naphthyl.

4. A compound according to claim 1, wherein R in formula I is unsubstituted or substituted by $C_1$–$C_4$alkyl, $C_1$–$C_4$alkoxy, $C_1$–$C_4$alkylthio, —F, —Cl, —Br or —COOR$_5$, wherein R$_5$ is H or $C_1$–$C_{18}$alkyl.

5. A compound according to claim 1, wherein R$_4$, or R$_1$ and either R$_3$ or R$_4$, or each of R$_1$ to R$_4$ is a group RO— or —Cl.

6. A compound according to claim 1, wherein R is unsubstituted phenyl.

7. A compound according to claim 1, wherein the compound of formula I is selected from the group consisting of 2,6,11-triphenoxynaphthacene-5,12-dione, and 2,3,6,8,9,11-hexaphenoxynaphthacene-5,12-dione.

8. A compound of formula V

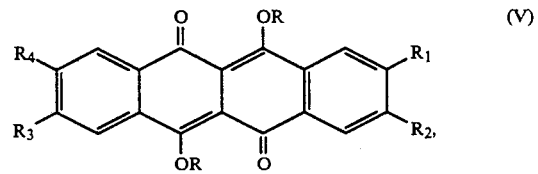

wherein

R is unsubstituted $C_6$–$C_{14}$aryl or $C_6$–$C_{14}$aryl which is substituted by $C_1$–$C_{12}$alkyl, $C_1$–$C_{12}$alkoxy, $C_1$–$C_{12}$alkylthio, phenyl, benzyl, —CN, —CF$_3$, halogen or —COOR$_5$, and R$_5$ is H, $C_1$–$C_{18}$alkyl, cyclohexyl, cyclopentyl, phenyl, $C_1$–$C_{12}$alkylphenyl, benzyl or $C_1$–$C_{12}$alkylbenzyl, and at least one of the substituents R$_1$ to R$_4$ is —F, —Cl or —Br, or is independently the group RO—, and the other substituents R$_1$ to R$_4$ are H, —F, —Cl or —Br, or a mixture thereof.

9. The compound 6,11-diphenoxy-2,3,8,9-tetrachloronaphthacene-5,12-dione.

* * * * *